(12) United States Patent
Wessels et al.

(10) Patent No.: US 7,276,172 B2
(45) Date of Patent: Oct. 2, 2007

(54) METHOD FOR PREPARING A NANOWIRE CROSSBAR STRUCTURE AND USE OF A STRUCTURE PREPARED BY THIS METHOD

(75) Inventors: Jurina Wessels, Stuttgart (DE); William E. Ford, Stuttgart (DE); Akio Yasuda, Stuttgart (DE)

(73) Assignee: Sony Deutschland GmbH, Cologne (DE)

( * ) Notice: Subject to any disclaimer, the term of this patent is extended or adjusted under 35 U.S.C. 154(b) by 303 days.

(21) Appl. No.: 10/636,843

(22) Filed: Aug. 7, 2003

(65) Prior Publication Data

US 2004/0028812 A1 Feb. 12, 2004

(30) Foreign Application Priority Data

Aug. 8, 2002 (EP) ................... 02017716

(51) Int. Cl.
*C23F 1/00* (2006.01)
(52) U.S. Cl. .......................... 216/2; 977/943
(58) Field of Classification Search ..................... None
See application file for complete search history.

(56) References Cited

U.S. PATENT DOCUMENTS

| | | | | |
|---|---|---|---|---|
| 5,475,341 A * | 12/1995 | Reed | .......................... | 327/566 |
| 5,723,320 A * | 3/1998 | Dehlinger | .................. | 435/91.1 |
| 6,128,214 A | 10/2000 | Kuekes et al. | | |
| 6,248,674 B1 * | 6/2001 | Kamins et al. | ............. | 438/798 |
| 6,294,450 B1 * | 9/2001 | Chen et al. | .................. | 438/597 |
| 6,657,884 B2 * | 12/2003 | Bocian et al. | ............... | 365/151 |
| 6,728,129 B2 * | 4/2004 | Lindsey et al. | ............. | 365/151 |
| 6,760,245 B2 * | 7/2004 | Eaton et al. | ................. | 365/100 |
| 6,777,516 B2 * | 8/2004 | Li et al. | ...................... | 526/258 |
| 6,781,166 B2 * | 8/2004 | Lieber et al. | ................ | 257/211 |
| 6,812,117 B1 * | 11/2004 | Tringe | ........................ | 438/466 |
| 6,872,645 B2 * | 3/2005 | Duan et al. | .................. | 438/584 |
| 6,900,479 B2 * | 5/2005 | DeHon et al. | .............. | 257/202 |
| 6,919,592 B2 * | 7/2005 | Segal et al. | .................. | 257/209 |
| 6,942,921 B2 * | 9/2005 | Rueckes et al. | ............ | 428/408 |
| 2001/0054709 A1 * | 12/2001 | Heath et al. | .................. | 257/25 |

(Continued)

FOREIGN PATENT DOCUMENTS

DE  199 41 448  3/2001

(Continued)

OTHER PUBLICATIONS

Yu Huang et al: "Directed Assembly of One-Dimensional Nanostructures Into Functional Networks", Science, Jan. 26, 2001, American Assoc. Adv. Sci, USA, vol. 291, No. 5504, pp. 630-633, XP002226671.

*Primary Examiner*—Allan Olsen
(74) *Attorney, Agent, or Firm*—Oblon, Spivak, McClelland, Maier & Neustadt, P.C.

(57) ABSTRACT

The present invention relates to a method for preparing a nanowire crossbar structure, comprising: (a) providing a substrate; (b) depositing thereon a composite structure comprising a nucleic acid-block copolymer having equidistant nucleic acid-catalyst binding sites and at least one catalyst nanoparticle functionalized to bind specifically to nucleic acid segments of the copolymer; (c) applying a directed gas flow and/or an alternating electric field onto the composite structure; and (d) applying chemical vapor deposition techniques, a use of such a structure and a structure obtainable by such a method.

29 Claims, 4 Drawing Sheets

U.S. PATENT DOCUMENTS

| | | | |
|---|---|---|---|
| 2002/0113229 A1* | 8/2002 | Bratkovski et al. | 252/500 |
| 2002/0176276 A1* | 11/2002 | Zhang et al. | 365/151 |
| 2003/0027195 A1* | 2/2003 | Ford et al. | 435/6 |
| 2003/0082444 A1* | 5/2003 | Kuhr et al. | 429/149 |
| 2003/0089899 A1* | 5/2003 | Lieber et al. | 257/9 |
| 2004/0004485 A1* | 1/2004 | Lee et al. | 324/658 |
| 2004/0005258 A1* | 1/2004 | Fonash et al. | 422/271 |
| 2004/0005723 A1* | 1/2004 | Empedocles et al. | 438/1 |
| 2004/0041617 A1* | 3/2004 | Snider et al. | 327/365 |
| 2004/0110350 A1* | 6/2004 | Pang et al. | 438/299 |
| 2004/0114445 A1* | 6/2004 | Occhipinti et al. | 365/202 |
| 2004/0115524 A1* | 6/2004 | Misra et al. | 429/160 |
| 2004/0127025 A1* | 7/2004 | Crocker et al. | 438/677 |
| 2004/0257736 A1* | 12/2004 | Goldstein et al. | 361/93.1 |

FOREIGN PATENT DOCUMENTS

| | | |
|---|---|---|
| EP | 1 209 695 | 5/2002 |
| WO | WO 01 03208 | 1/2001 |

\* cited by examiner

METHOD FOR PREPARING A NANOWIRE CROSSBAR STRUCTURE AND USE OF A STRUCTURE PREPARED BY THIS METHOD

The present invention relates to a method for preparing a nanowire crossbar structure, to the use of a structure prepared by this method, and to a structure obtainable by such a method.

Nanowires are wires exhibiting a diameter in the range of about 1 nm to about 500 nm. They can be fabricated from metal or from semi-conductor material. Different synthesis routes for semi-conducting nanowires using vapor or solution based methods have been described, for example by Gudiksen, M. S. (2000), J. Am. Chem. Soc., 122, 8801-8802, and Trentler, T. J. (1995), Science, 1791-1793. A key factor for promoting anisotropic crystal growth in these synthetic routes is utilizing metal nanoparticles as catalysts. In case of the vapor based growth process, the growth mechanism is described in the literature in terms of a vapor-liquid-solid growth mechanism. In case of the solution based growth process, the growth can be described as a solution-liquid-solid phase process.

The vapor-liquid-solid growth process consists of three phases (I) metal alloying, (II) crystal nucleation, and (III) axial growth, see for example Wu, Y. (2001) J. Am. Chem. Soc., 123, 3165-3166. In the alloying phase, the metal clusters remain at first in the solid phase and the inorganic semi-conducting material is evaporated. The vapor starts to condense on the metal cluster surfaces and leads to the formation of an alloy and liquefies. With increasing vapor condensation the size of the droplet increases and the growth process enters the second phase. The co-existence of the metal/semi-conductor alloy and a crystalline phase of the semi-conductor characterizes this phase. The nucleation of the nanowires starts during this phase. After nucleation of the wire, further vapor condensation and dissolution during the third phase leads to the growth of the nanowire. The diameter of the nanowire can be controlled by the size of the nanoparticle.

Synthetic routes for the fabrication of different types of semi-conducting nanowires have been described in the literature and are known to persons skilled in the art. The predictable synthesis of a broad range of binary and ternary III-V, II-VI and IV-IV group semi-conductor nanowires has been reported, using the laser assisted catalytic growth method. It has been shown that the semi-conducting nanowires can also be doped with different types of dopants, see Duan, X. (2001), Nature, 409, 66-69. Doping influences the charge transport through the wire. Depending on the type of dopant the wire can have n-type or p-type characteristics.

In addition, the synthesis of carbon nanowires is described in detail, for example, in Ebbesen, T. W. (1997), "Carbon Nanotubes: Preparation and Properties", CRC Press. Depending on the chirality of the C-nanowires, they can be either metallic or semi-conducting. Single-wall carbon nanotubes synthesised by the catalytic decomposition of carbon monoxide and ethylene over a supported metal catalyst can exhibit diameters between 0.5 mm and 3 mm, see Hafner, J. H. (1998), Chemical Physics Letters 296, 195-202. Further, it has been shown that semi-conducting C-nanowires can be doped so that they exhibit either p- or n-type characteristics.

The chemical modification of nanowires along the longitudinal direction of the wires is also described in the literature. Via these modifications specific chemical groups can be attached along the nanowire. These groups can be used, for example for immobilizing the nanowires onto surfaces, see Bahr, J. L. (2001), J. Am. Chem. Soc., 123, 6536-6542.

It has been shown that crossbar structures of nanowires can be used as electrically addressable passive devices for storage and processing of data. Nanowires that have been used to demonstrate device characteristics are, for example, p- and n-doped semiconducting nanowires or C-nanowires, see Huang, Y. (2001), Science, 291, 630-633, and Rueckes, T. (2000), Science, 289, 94-97. In all cases the arrays contained between 2 and 6 nanowires, which were assembled using a PDMS stamp in combination with hydrodynamic alignment. The electrode contacts were evaporated on top of the assembled nanowires. The fabrication methods mentioned, however, cannot be used for the fabrication of large addressable arrays of nanowires that can be used for the fabrication of future nanoscale electronic circuits.

Several patents have been published that describe the fabrication of nanowire arrays, for example U.S. Pat. Nos. 6,231,744, 6,159,831, EP 1 104 011 and U.S. Pat. No. 6,055,180. Amongst the techniques that are described for the fabrication of quantum wires, one approach involves filling of arrays of nanochannels or pores in a substrate, such as for example anodic alumina. The problem with this method is that pores or nanochannels often merge within the substrate. Also, the formation of long nanowires is difficult. Further, it is difficult to fill the pores homogeneously with different materials, and no technique is available with which the diameter, length, and packing density of the pores in anodic alumina can be controlled. In U.S. Pat. No. 6,231,744 a solution is provided which still relies on the pore filling strategy, but allows for fabricating a substrate having a plurality of non-interconnected wires, the diameter of which does not vary by more than 100%. Another pore-filling concept is also described in U.S. Pat. No. 6,159,831. EP 1 104 011 focusses on the fabrication of nanowire arrays based on silicon nano structures. Silicon surfaces are sputtered with $N_2$ to create a wave-like relief structure on the surface. A mask is used to define the location of the array. A very general description of how to achieve the formation of an array structure can be found in U.S. Pat. No. 6,055,180. Here, it is only mentioned that the electrically addressable passive device shall be realized with a functional medium in the form of an organic material.

One major problem in the fabrication of nanowire crossbar structures in the prior art is to obtain 2-D nanowire structures with regular spacing between the wires on non-structured surfaces. A prerequisite for achieving this is the equidistant placement of catalyst nanoparticles on the surfaces. One possibility of achieving this is described in WO 01/03208. In this patent the equidistant placement of catalyst nanoparticles is achieved via chemical modification of a self-assembled monolayer using either e-beam or scanning probe techniques. However, this solution still requires the use of expensive high resolution e-beam or scanning probe techniques and it is desirable to provide a solution where regularly spaced catalyst nanoparticles can be placed on the substrate via self-assembly.

DNA provides versatile assembly properties due to the specificity of base paring that hold the two strands together and the sticky ends that can be chemically modified. Possibilities for nucleic acid engineering and its application to nanotechnology is described by Seeman, N.C., (1999) TIBTECH17, 437. In addition it provides a variety of complexing or covalent binding sites along the strand and it can be custom made at any length. It has been shown that nano-particles can be well assembled into regular structures using DNA as a template. In these examples the nanoparticles were attached to the sticky ends of the DNA and the structures were assembled via sequence specific hybridisation processes, see for example Maeda. J. (2001), App. Phys. Lett.; 79, 1181.

It is an object of the present invention to provide a method for preparing a nanowire crossbar structure which overcomes the drawbacks associated with the prior art, especially to provide a method for preparing a nanowire crossbar structure having a parallel set of nanowires with a defined distance at a predetermined position.

The object is achieved by a method for preparing a nanowire crossbar structure, comprising: (a) providing a substrate; (b) depositing thereon a composite structure comprising a nucleic acid-block copolymer having equidistant nucleic acid-catalyst binding sites and at least one catalyst nanoparticle functionalized to bind specifically to nucleic acid segments of the copolymer; (c) applying a directed gas flow and/or an alternating electric field onto the composite structure; and (d) applying chemical vapor deposition techniques.

Preferably, the composite structure is attached by one or two of its ends to a substrate.

Preferably, the substrate prior deposition is processed by etching, wherein etching forms grooves into the substrate for receiving nanowires, the grooves having a diameter in the range of about 2 nm to about 40 nm, preferably about 2 nm to about 10 mm.

Further, the method comprises a nucleic-acid templated positioning of catalytic nucleation sites.

Preferably, the nanoparticle catalyst is attached to the nucleic acid blocks of the nucleic acid-block copolymer using a linker molecule comprising one or more nucleic acid binding group(s) and one or more nanoparticle binding group(s) which are connected covalently by a spacer group.

Alternatively, preformed nanoparticles are attached to the nucleic acid blocks of the nucleic acid-block copolymer.

Still alternatively, the nanoparticles are formed in-situ on the nucleic acid blocks of the nucleic acid-block copolymer.

In a further embodiment, the composite structure is treated with an electroless plating solution for precise size control while dissolved in solution, or attached by one or two of its ends to a substrate.

Preferably, the nucleic acid is selected from the group comprising DNA, RNA, PNA, CNA, oligonucleotides, oligonucleotides of DNA, oligonucleotides of RNA, primers, A-DNA, B-DNA, Z-DNA, polynucleotides of DNA, polynucleotides of RNA, T-junctions of nucleic acids, triplexes of nucleic acids, quadruplexes of nucleic acids and combinations thereof.

Further, the nucleic acid may be synthetic or natural.

Moreover, the nucleic acid is double-stranded or single-stranded.

Preferably, the non-nucleic acid blocks of the block copolymer are selected from the group of poly(ethyleneglycol) and/or poly(aminoacid).

Further, the non-nucleic acid blocks of the block copolymer comprise between 10 and 1,000 repeating units, preferably between 40 and 400 repeating units.

Furthermore, the catalyst nanoparticle comprises a metal or metal oxide in the core of the nanoparticle being selected from the group comprising Fe, Co, Ni, Au, Pt, Y, Mo, Ru, Pd, Ag, Cu, Zn, Mg, Al or combinations, especially alloys or mixed oxides, of these metals.

The shape of the catalyst nanoparticle may vary from essentially spherical to plate-like, but has a largest dimension in the range between 0.5 nm and 20 nm, preferably between 1 nm and 10 nm.

In one embodiment of the invention the substrate acts substantially as an insulator.

Preferably, the substrate has an electrical resistivity of at least about $10^{12}$ $\mu\Omega$ cm and a di-electric constant in the range between 1 and about 8.

It is also preferred that the substrate is made of $SiO_x$, $Si_3N_4$ and the like.

It is preferred that the nanowires have a diameter in the range of about 0.5 nm and about 20 nm, preferably about 0.5 nm and about 10 nm.

Furthermore, the nanowires are chemically modified along the longitudinal direction of the wires with specific chemical groups.

Preferably, the nanowires are immobilized onto the substrate by the chemical groups on the nanowire.

Still preferred, the nucleic acid-block copolymer is anchored to the surface of the substrate via covalent bond formation, such as amide, ester, ether, or urea bonds.

Moreover, the nanowire crossbar structure prepared according to the present invention may be used in an array, an electronic network, an electronic circuit or for recording, storage and processing of data.

Finally, according to the invention a nanowire crossbar structure may be provided which is obtainable by a method according to the present invention.

Surprisingly, it was found that according to the present invention nanowire crossbar structures may be prepared based on self-assembly processes using conventional, for example CVD and etching processes, in combination with nucleic acid-templated positioning of the catalytic nucleation sites. A nucleic acid-block copolymer composition structure is used for the positioning of the catalyst particles on the surface. The invention provides a solution for the self-assembly of nm-scale wires into crossbar structures at predetermined positions as memory devices or for signal routing and communication. Moreover, this invention provides a solution to a patterning method for the precursor catalysts by using composite structures as a template for the formation of linear chains of equidistant catalyst nanoparticles. The present invention facilitates the preparation of large addressable arrays of nanowires for use of nanoscale electronic circuits and defines the start point for the growth of nanowires by self-assembly.

The main difference to the pre-existing state of the art is that the present invention provides a solution to control the distance between the wires on the nm-scale by self-assembly methodologies.

The crossbar structure can be fabricated by two different routes.

In a first route, the bottom-layer is self-assembled from pre-formed wires onto a processed substrate and the top layer is grown from catalyst nanoparticles deposited onto the substrate. The substrate is prior to deposition of preformed wires processed by etching, wherein etching forms grooves in the substrates. The grooves have a depth and width in the range of about 2 nm to about 40 nm, preferably about 2 nm to about 10 nm. The profile of the grooves can have an isotropic or anisotropic shape. For the growth of the top layer, anchor points are patterned onto the substrate for the deposition of the nucleic acid-block copolymer. The anchor groups may be patterned using, e.g. micro contact printing, scanning-probe, or e-beam based modifications of surface groups that have been self-assembled onto the substrate. The nucleic acid-block copolymer may be anchored to the surface of the substrate through covalent bond formation via amide, ester, ether, or urea bonds. The anchor groups are deposited in such a way that the nucleic acid-block copolymer is oriented at an angle of 45° to 135° relative to the grooves, preferably at 90°.

In a second route, both layers of the crossbar structure are grown from catalyst particles deposited onto the substrate via the nucleic acid block-copolymer structure. In this case the anchor points for the attachment of the first composite structure are prepared prior to the growth process of the first layer. After the growth process of the first layer is accomplished the anchor points for attaching the nucleic acid-block copolymer are deposited onto the substrate in such a way that the nucleic acid-block copolymer is oriented at an angle of 45° to 135° relative to the orientation of the first layers of tubes, preferably at 90°.

The invention will now be described in a further detail by illustrative examples with respect to the accompanying drawings in which FIG. 1 shows a nucleic acid-block copolymer structure for use in the method according to the present invention;

Figure 1:
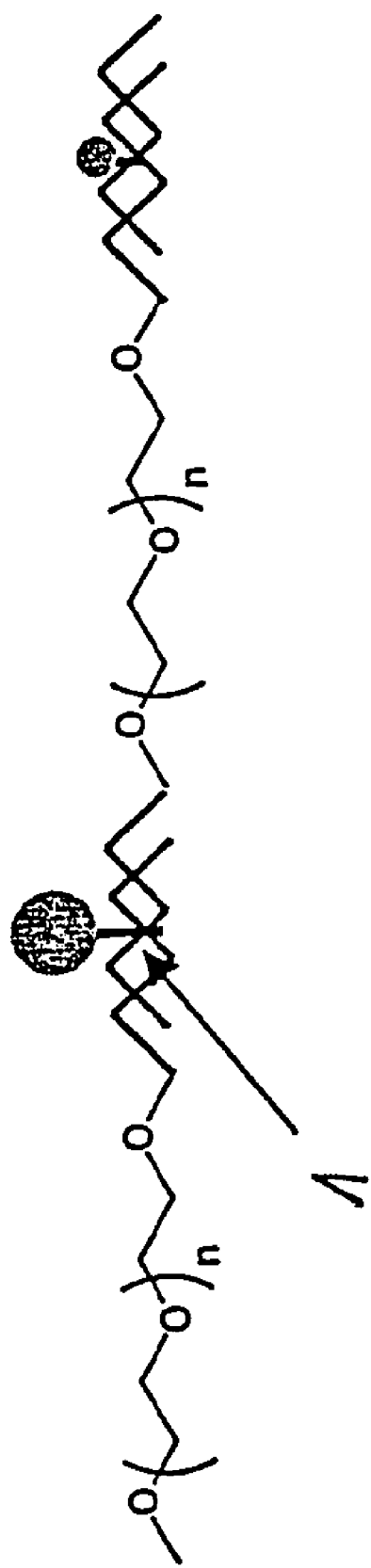
Figure 2:
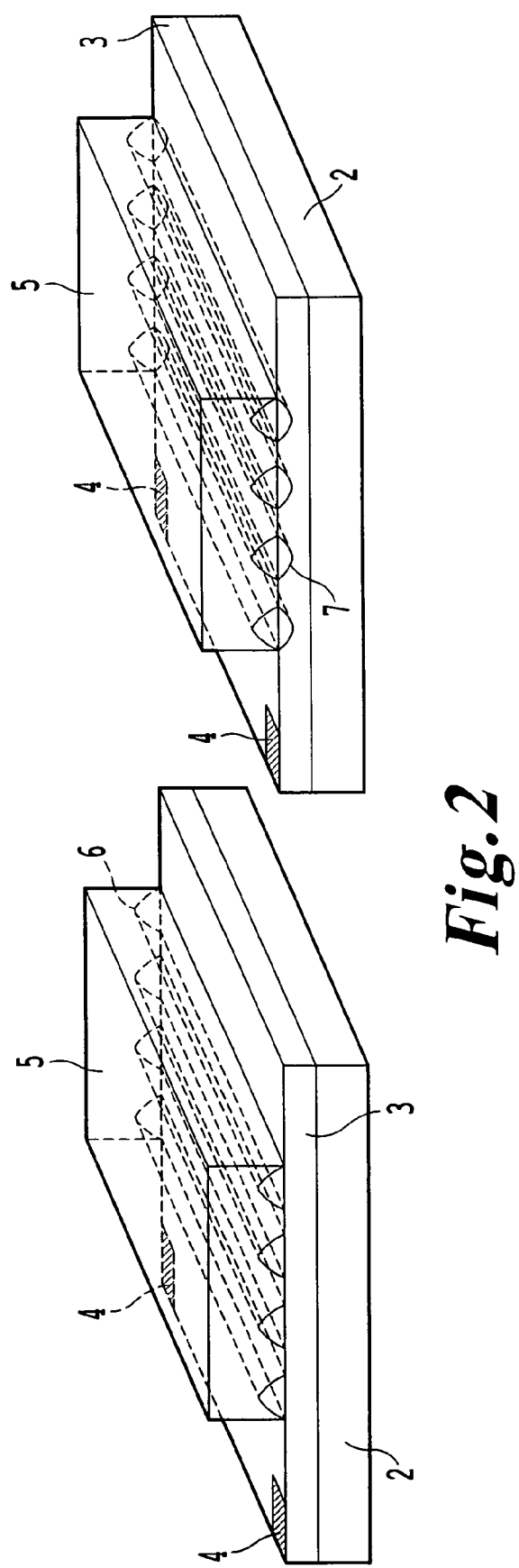
FIG. 2 shows a substrate preparation route for preparing a nanowire crossbar structure according to the present invention.

One embodiment of a method for the preparation of nanowire crossbar structures via self-assembly is outlined in FIGS. 1-3. In general, three primary components are involved in the process: (1) a nucleic acid-block copolymer having equidistant nucleic acid catalyst binding sites, (2) a catalyst nanoparticle functionalised to bind specifically to nucleic acid segments of the copolymer, and (3) a substrate onto which the composite structure is attached.

The composite structure is used for positioning the catalyst nanoparticles on the substrate with regular defined distances between them. The catalyst nanoparticles are bound selectively to the nucleic acid blocks in the copolymer, while the distance between the catalyst particles is determined by the length of the non-nucleic acid block, e.g. poly(ethylene glycol) or poly(amino acid). FIG. 1 shows, as an example, a nucleic acid-block copolymer structure with poly(ethylene glycol) as non-nucleic acid blocks. The nucleic acid block comprises a reactive site 1 for selective attachment of a seed particle to nucleic acid. With n=40 the poly(ethylene glycol) block has a length of about 15 nm. With n=400, the poly(ethylene glycol) block has a length of about 150 nm, wherein the length distribution can be adjusted to be ±0.35 nm. The diameter of the composite structure shown in FIG. 1 is about 2 nm.

A straightforward way to synthesise block copolymers used in this invention is to covalently couple the pre-formed blocks, i.e., the nucleic acid block with the non-nucleic acid block. In the case of poly(ethylene glycol) (PEG), derivatives of various lengths with amino groups (—$NH_2$) at both ends are commercially available. These amino groups can be condensed with the 5'-phosphate groups present at each end of, for example, double-stranded DNA (ds-DNA) to form stable phosphoramidate bonds by using a condensing agent such as a water-soluble carbodiimide, see Hermanson, G. T. (1996), Bioconjugate Techniques, Academic Press, London, Chapter 17. The bond linkages and stoichiometry involved in the synthesis of such a DNA-PEG block copolymer is indicated in equation (1):

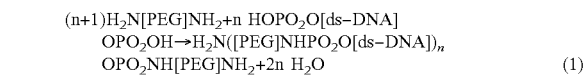

A slight molar excess of the bis-amino-PEG block relative to the ds-DNA block is used so that both ends of the block copolymer have —$NH_2$ groups for attachment to the substrate. The $H_2O$ indicated as a product actually adds to the carbodiimide to form a urea. The spontaneous polymerization of α-amino acid N-carboxyanhydrides (NCAs) initiated by diamino-substituted compounds can generate polypeptide blocks of uniform lengths with amino groups at both ends, see Fontaine, L. (2001), Reactive & Functional Polymers, 47, 11-21. Alternatively, the polypeptide blocks can be initiated with diamino-substituted compounds in which one of the amino groups is protected, then de-protecting the amino group to obtain polypeptide blocks with amino groups at both ends. These blocks can likewise be condensed with ds-DNA via its 5'-phosphate ends.

The catalyst nanoparticles can be attached to the nucleic acid blocks of the nucleic acid-block copolymer in a number of ways that are nucleic acid specific. If pre-formed nanoparticles are being used, the nucleic acid-binding groups can be included in the ligand shell (capping molecules) of the nanoparticle. Such groups may include intercalation agents, groove-binding agents, alkylating agents, and triple-strand forming oligonucleotides. This strategy is, for example, described in the patent application EP 00126966.1 where the linker molecule comprises one or more nucleic acid binding group(s) and one or more nanoparticle binding group(s) connected covalently by a spacer group. Another route for binding pre-formed metal nanoparticles ex-situ to nucleic acids via the ligand shell is described in EP 01118920.6. Alternatively, metal nanoparticles can be generated in-situ as described in EP 1 209 695 A. In all cases, the nature of the catalyst depends on the type of nanowire to be formed. A few examples reported in the literature are summarised in the table below. The diameter of the particle in the preferred embodiment of this invention is preferably in the range between 0.5 nm and 10 nm. A direct correlation has been observed between the diameter of metal catalysts and the diameter of carbon nanowires grown there from, see Cheung, C. L. (2002), J. Phys. Chem. B, 106, 2429. The wires composed of III/V and II/VI materials are grown using the laser assisted catalytic growth process (LCG).

| | Catalyst particle | reactant flow |
|---|---|---|
| Nanowires | | |
| Si | Au | $SiH_4$ |
| Ge | Au | Ge |
| Silicon carbide | Au | $SiH_4$ |
| Gallium nitride | Fe | $SiH_4$ |
| Gallium nitride | $Fe_2O_3$ | (Ga-oxide and $NH_3$ vapor) |
| C-nanowires | Fe | $C_2H_2$ |
| C-nanowires | Ni | mixture of $CH_4/H_2$ |
| C-nanowires | formed from ferritin | $C_2H_2$ |
| III/V wires | | |
| GaAs | Au/Ag/Cu/Co/Pt | $Ar/H_2$ |
| GaP | Au | $Ar/H_2$ |
| GaAsP | Au | $Ar/H_2$ |
| InAs | Au | $Ar/H_2$ |

-continued

| | Catalyst particle | reactant flow |
|---|---|---|
| InP | Au | Ar/H$_2$ |
| InAsP | Au | Ar/H$_2$ |
| II/VI wires | | |
| ZnSe | Au | Ar/H$_2$ |
| CdS | Au | Ar/H$_2$ |
| CdSe | Au | Ar/H$_2$ |

The third component necessary for the growth process is a substrate that is prepared in such a way that a suspended crossbar structure can be assembled using the above-described composite structure.

Two routes for the self-assembly process are possible: (a) the bottom layer of wires is self-assembled onto the processed substrate and catalyst nanoparticles for the growth of the top-layer are subsequently assembled onto the substrate, (b) both layers of wires are grown on the substrate from catalyst particles that have been assembled via nucleic acid-block copolymer structures onto the substrate. In the ideal situation, the substrate should be comprised out of a material with sufficient insulating properties. Preferably, the substrate is composed of an electrically insulating material with a resistivity larger than $10^{12}$ μΩ cm. Further, the dielectric constant ε of the substrate should be in the regime $1 < \epsilon < 8$. However, it is also possible that the grooves are etched into conductive materials such as metals, for example, and subsequently an insulating layer such as SiO$_x$ can be evaporated onto the etched structure.

FIG. 2 shows a substrate preparation route for a nanowire crossbar structure according to the invention. In the left part of FIG. 2 a substrate 2 comprising a surface layer 3 is shown. Preferably, the substrate is silicon. On the surface layer 3 are anchor points 4 for the composite structure. Further, on the surface layer 3 a stamp 5 is provided having capillaries 6 on its underside. By injection of etching solution into the pores via capillary forces grooves 7 may be formed after the etching process, as is shown on the right part of FIG. 2. The groove profile and the depth may be controlled via the etch rate.

Figure 3A:
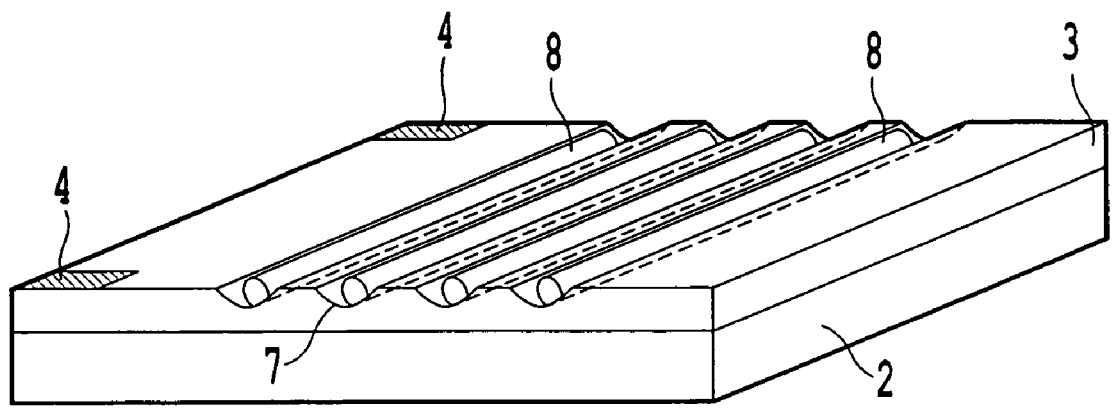
FIG. 3a shows a further detail of the substrate preparation route.

For the growth of a crossbar structure it is preferable to etch a groove structure into the substrate, as shown in FIG. 3a. This groove structure will be used as a template to assemble the first layer using pre-formed nanowires 8. The nanowires 8 can be assembled into the grooves 7 using a hydrodynamic alignment procedure. The required size of the grooves 7 depends on the diameter of the nanowires, ranging from 2 nm to 40 nm, preferably in the range between 2 nm and 10 nm. The grooves 7 can be prepared by wet-etching or dry-etching techniques aiming for an isotropic or anisotropic etching profile. Generally it is important that the groove is deeper than the diameter of the wire, so that the second layer of wires is not in direct contact with the first layer. In case an insulating layer is evaporated on top of the etched layer, the groove to groove distances and the grooved depth has to be adjusted accordingly. For the dry etching processes, focussed ion beam radiation can, for example, be used. The groove diameter and the groove to groove distance in this case is limited to about 50 nm, depending on the diameter of the ion beam. Alternatively a wet-etching technique may be used to form regularly spaced grooves on the substrate. In this case, depending on the material of the substrate surface, the etching process is based on water or on acidic or basic solvent mixtures.

For the formation of a regular pattern of grooves 7 into the substrate 2, a fluidic channel system can be used to limit the etching process to pre-defined areas on the substrate 2. The material that is used for the preparation of the fluidic channels depends on the etching process and on the desired groove size. Generally fluidic channels can be prepared by conventional soft-lithographic techniques, such as replica molding (limit 30 nm), solvent-assisted micro-contact molding (limit 60 nm), micro-transfer molding (limit 250 nm), and micro-contact printing (limit 300 nm), Alternatively it is also envisioned that instead of grooves 7, continuous insulating channels are formed on the substrate 2 using one of the techniques mentioned above.

Figure 3B:
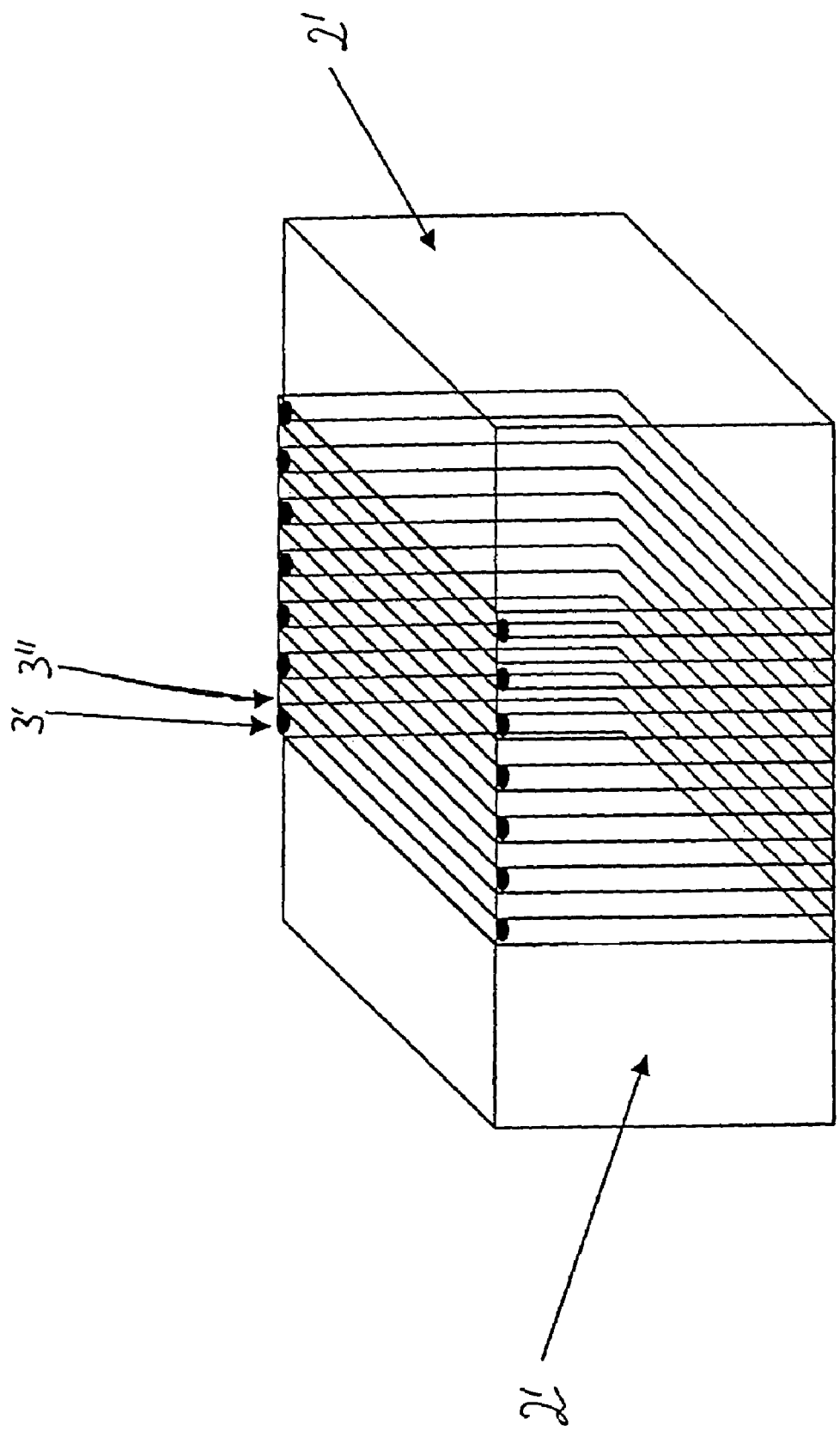
FIG. 3b shows another embodiment of the substrate preparation route.

A further possibility for forming narrow channels is to use a sandwich substrate 2' that contains alternating thin layers 3', 3" of two materials exhibiting different etching properties, shown in FIG. 3b. In this way, the width of the grooves etched into the substrate 2' is determined by the thickness of the layer 3', 3" in the sandwich structures as indicated in FIG. 3b.

In a second step the nucleic acid-block copolymer (or the copolymer/catalyst nanoparticle composite) is attached to the surface 3, 3', 3" via chemically functional anchor groups that are patterned onto the surface. The anchor groups for the attachment of the nucleic acid-block copolymer to the surface can be patterned e.g. via micro contact printing or optical/e-beam lithography. Covalent attachment of nucleic acid-block copolymers having NH$_2$ groups at each end, such as the ones described above, to carboxylic acid (—COOH) anchor groups can be achieved by using coupling agents such as carbodiimide to promote amide bond formation.

Stretching of the composite structure can be achieved by applying either a hydrodynamic flow or an electric field for example.

The features disclosed in the foregoing description, in the claims and/or in the accompanying drawings may, both separately and in any combination thereof, be material for realizing the invention in diverse forms thereof.

The invention claimed is:

1. A method for preparing a nanowire crossbar structure, comprising:
   forming a composite structure on a substrate, the composite structure comprising a nucleic acid-block copolymer having equidistant nucleic acid-catalyst binding sites and at least one catalyst nanoparticle functionalized to bind specifically to at least one of the nucleic acid-catalyst binding sites; and
   growing at least one nanowire from the at least one catalyst nanoparticle as part of the nanowire crossbar structure;
   wherein:
   the substrate is etched to form grooves for receiving nanowires prior to forming the composite structure on the substrate; and
   the grooves are formed to a diameter of from about 2 nm to about 40 nm.

2. The method according to claim 1, wherein the composite structure is attached by one or two of its ends to the substrate.

3. The method according to claim 1, wherein:
   the at least one catalyst nanoparticle is attached to the at least one of the nucleic acid-catalyst binding sites by a linker molecule;
   the linker molecule comprises at least one nucleic acid binding group and at least one nanoparticle binding group, the binding groups being connected covalently by a spacer group.

4. The method according to claim 1, wherein the composite structure is formed by attaching preformed catalyst nanoparticles to nucleic acid blocks of the nucleic acid-block copolymer.

5. The method according to claim 1, wherein the composite structure is formed by forming catalyst nanoparticles on nucleic acid blocks of the nucleic acid block copolymer in situ.

6. The method according to claim 1, wherein the composite structure is treated with an electroless plating solution for precise size control while dissolved in solution, or attached by one or two of its ends to a substrate.

7. The method according to claim 1, wherein the nucleic acid block copolymer comprises a nucleic acid selected from the group consisting of DNA, RNA, PNA, CNA, oligonucleotides, oligonucleotides of DNA, oligonucleotides of RNA, primers, A-DNA, B-DNA, Z-DNA, polynucleotides of DNA, polynucleotides of RNA, T-junctions of nucleic acids, triplexes of nucleic acids, quadruplexes of nucleic acids and combinations thereof.

8. The method according to claim 1, wherein the nucleic acid block copolymer comprises a synthetic nucleic acid.

9. The method according to claim 1, wherein the nucleic acid block copolymer comprises a double-stranded nucleic acid.

10. The method according to claim 1, wherein the at least one catalyst nanoparticle has a core comprising at least one member selected from the group consisting of Fe, Co, Ni, Au, Pt, Y, Mo, Ru, Pd, Ag, Cu, Zn, Mg, Al, combinations thereof, alloys thereof, oxides thereof and mixed oxides thereof.

11. The method according to claim 1, wherein the nanowires are formed to a diameter of from about 0.5 nm to about 20 nm.

12. The method according to claim 1, wherein the nucleic acid-block copolymer is anchored to a surface of the substrate via covalent bond formation.

13. The method according to claim 1, further comprising applying a directed gas flow onto the composite structure before forming the at least one nanowire.

14. The method according to claim 1, further comprising applying an alternating electric field onto the composite structure before forming the at least one nanowire.

15. The method according to claim 1, further comprising applying a directed gas flow and an alternating electric field onto the composite structure before forming the at least one nanowire.

16. The method according to claim 1, wherein the grooves are formed to a diameter of from about 2 nm to about 10 nm.

17. The method according to claim 1, wherein the nucleic acid block copolymer comprises a natural nucleic acid.

18. The method according to claim 1, wherein the nucleic acid block copolymer comprises a single-stranded nucleic acid.

19. The method according to claim 1, wherein the nucleic acid block copolymer comprises poly(ethyleneglycol) non-nucleic acid blocks.

20. The method according to claim 1, wherein the nanowires are formed to a diameter of from about 0.5 nm to about 10 nm.

21. The method according to claim 1, wherein the nucleic acid-block copolymer is anchored to a surface of the substrate via amide, ester, ether, or urea bonds.

22. The method according to claim 1, wherein the nucleic acid block copolymer comprises non-nucleic acid blocks selected from the group consisting of poly(ethyleneglycol) and poly(aminoacid).

23. The method according to claim 22, wherein the non-nucleic acid blocks comprise between 10 and 1,000 repeating units.

24. The method according to claim 23, wherein the non-nucleic acid blocks comprise between 40 and 400 repeating units.

25. The method according to claim 1, wherein the substrate acts substantially as an insulator.

26. The method according to claim 25, wherein the substrate has an electrical resistivity of at least about $10^{12}$ $\mu\Omega$ cm and a dielectric constant of between 1 and about 8.

27. The method according to claim 25, wherein the substrate comprises $SiO_x$, or $Si_3N_4$.

28. The method according to claim 1, wherein the nanowires are chemically modified with specific chemical groups along a longitudinal direction of the nanowires.

29. The method according to claim 28, wherein the nanowires are immobilized on the substrate via the specific chemical groups on the nanowire.

* * * * *